(12) United States Patent  
Kim et al.

(10) Patent No.: US 11,015,856 B2
(45) Date of Patent: May 25, 2021

(54) REFRIGERATOR AND METHOD OF CHANGING A DEODORIZING MODE ACCORDING TO A DETECTED SMELL

(71) Applicant: LG ELECTRONICS INC., Seoul (KR)

(72) Inventors: Eunjeong Kim, Seoul (KR); Jeongyon Kim, Seoul (KR); Yoojin Jung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 416 days.

(21) Appl. No.: 15/760,871

(22) PCT Filed: Sep. 16, 2016

(86) PCT No.: PCT/KR2016/010391
§ 371 (c)(1),
(2) Date: Mar. 16, 2018

(87) PCT Pub. No.: WO2017/048084
PCT Pub. Date: Mar. 23, 2017

(65) Prior Publication Data
US 2018/0274839 A1 Sep. 27, 2018

(30) Foreign Application Priority Data

Sep. 16, 2015 (KR) .................. 10-2015-0131229

(51) Int. Cl.
*F25D 17/04* (2006.01)
*A61L 9/01* (2006.01)
(Continued)

(52) U.S. Cl.
CPC ............ *F25D 17/042* (2013.01); *A61L 9/014* (2013.01); *A61L 9/122* (2013.01); *A61L 9/18* (2013.01);
(Continued)

(58) Field of Classification Search
CPC ......... F25D 2317/0415; F25D 2600/02; F25D 2700/00; A61L 9/00; A61L 2209/11; A61L 2209/111; A61L 2209/14; A61L 2209/22

See application file for complete search history.

(56) References Cited

U.S. PATENT DOCUMENTS 5,078,971 A 1/1992 Matuda et al.
2003/0235516 A1* 12/2003 Osawa et al. ...... G01N 33/0027
422/88

(Continued)

FOREIGN PATENT DOCUMENTS

CN 102741633 10/2012
CN 104101167 10/2014
(Continued)

OTHER PUBLICATIONS

Chinese Office Action dated Dec. 24, 2019 issued in Application No. 201680066962.4.

(Continued)

*Primary Examiner* — Edward F Landrum
*Assistant Examiner* — Daniel C Comings
(74) *Attorney, Agent, or Firm* — KED & Associates LLP

(57) ABSTRACT

A refrigerator may include a smell sensor for detecting smell in the refrigerator; a deodorizer for adsorbing, sterilizing, and deodorizing air in the refrigerator; and a controller for calculating smell values based on the detected smell at the smell sensor, changing a deodorizing mode according to the detected smell, and controlling the deodorizer.

32 Claims, 10 Drawing Sheets

(51) Int. Cl.
  *A61L 9/12* (2006.01)
  *F25D 29/00* (2006.01)
  *A61L 9/014* (2006.01)
  *A61L 9/18* (2006.01)

(52) U.S. Cl.
  CPC ......... *F25D 29/00* (2013.01); *A61L 2209/111* (2013.01); *A61L 2209/12* (2013.01); *A61L 2209/14* (2013.01); *A61L 2209/22* (2013.01); *F25D 2317/0415* (2013.01)

(56) References Cited

U.S. PATENT DOCUMENTS

| | | | |
|---|---|---|---|
| 2007/0266725 A1 | 11/2007 | Anikhindi et al. | |
| 2013/0015753 A1* | 1/2013 | Son | B01D 46/00 312/405 |
| 2014/0182315 A1* | 7/2014 | Kim | F25C 5/08 62/73 |
| 2014/0298835 A1* | 10/2014 | Choi | B01J 20/3236 62/125 |
| 2015/0018979 A1* | 1/2015 | Tomii | H04L 12/2803 700/19 |
| 2015/0143825 A1* | 5/2015 | Qu | F25D 21/004 62/80 |

FOREIGN PATENT DOCUMENTS

| | | |
|---|---|---|
| EP | 0 397 145 | 11/1990 |
| JP | S6470681 | 3/1989 |
| JP | H01302090 | 12/1989 |
| JP | H01306791 | 12/1989 |
| JP | 2003-172565 | 6/2003 |
| JP | 2007-170773 | 7/2007 |
| KR | 10-1999-0053425 | 7/1999 |
| KR | 20-0367856 U | 11/2004 |
| KR | 10-2008-003670 | 1/2008 |
| KR | 10-2008-0065407 | 7/2008 |
| KR | 10-2012-0022315 | 3/2012 |
| KR | 10-2012-0075825 | 7/2012 |

OTHER PUBLICATIONS

European Search Report dated Apr. 23, 2019 issued in Application No. 16846905.4.

International Search Report and Written Opinion dated Jan. 20, 2017 issued in Application No. PCT/KR2016/010391 (Full English Text).

Korean Notice of Allowance dated Sep. 17, 2018 issued in Application No. 10-2017-0077497.

* cited by examiner

[Fig. 1]
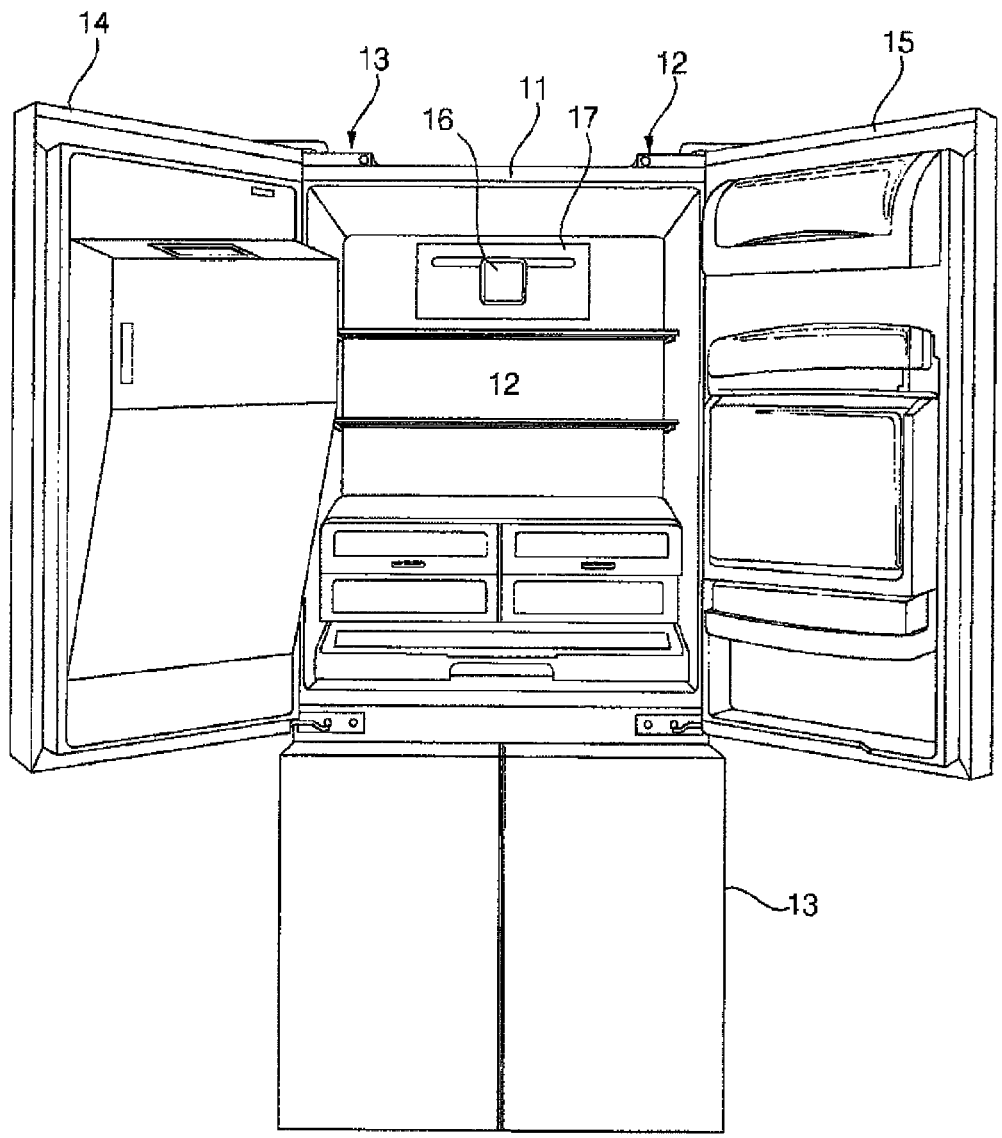

[Fig. 2]
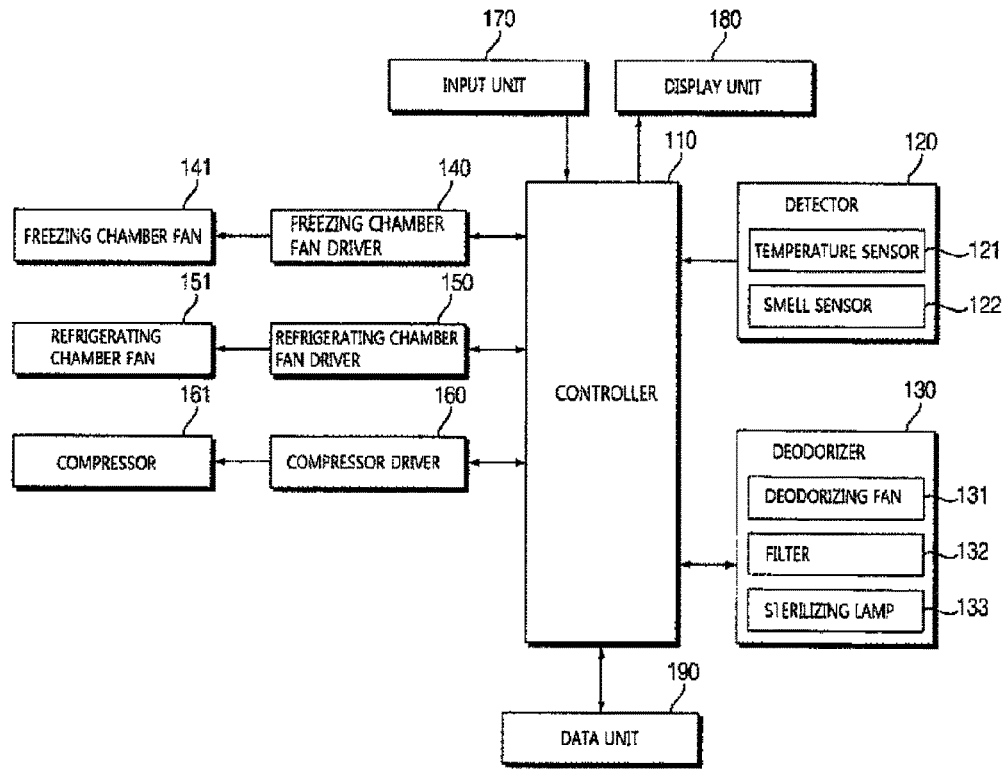
[Fig. 3]
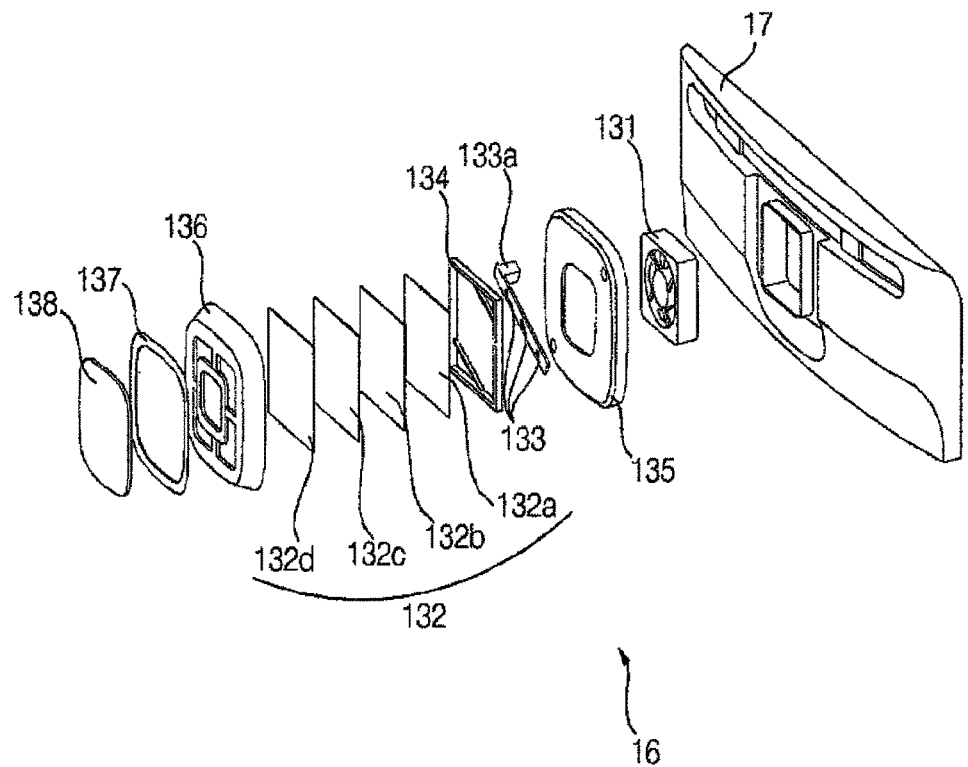

[Fig. 4]
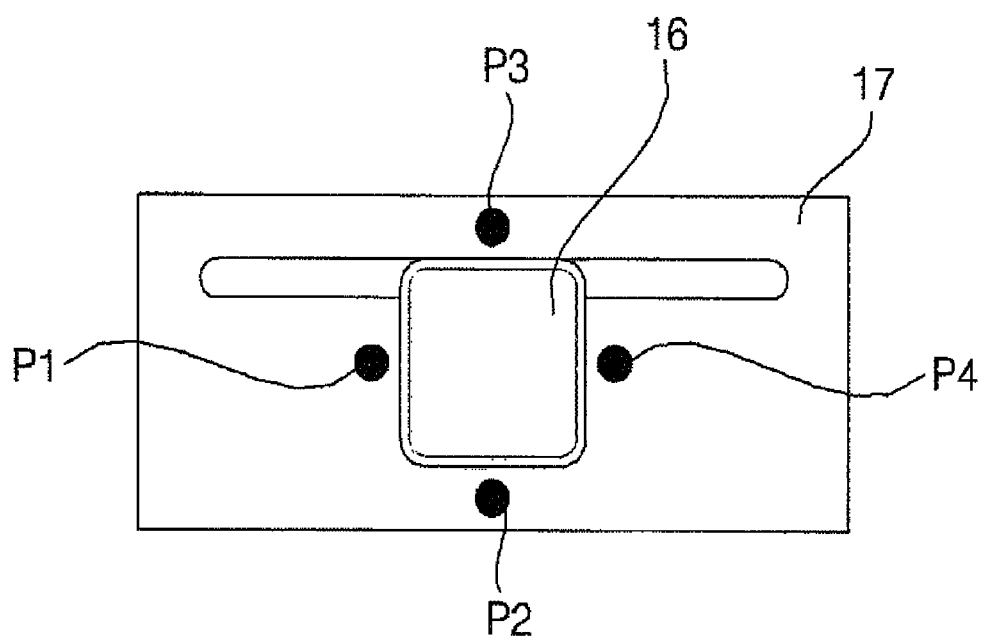

[Fig. 5]
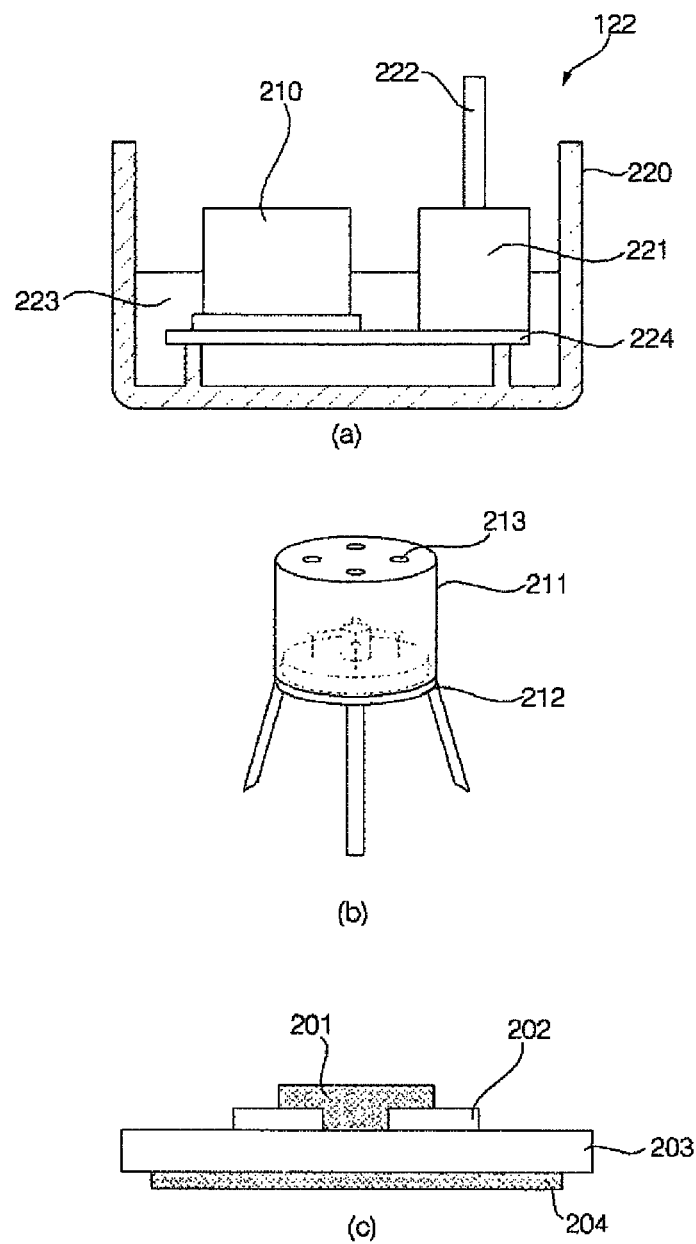

[Fig. 6]
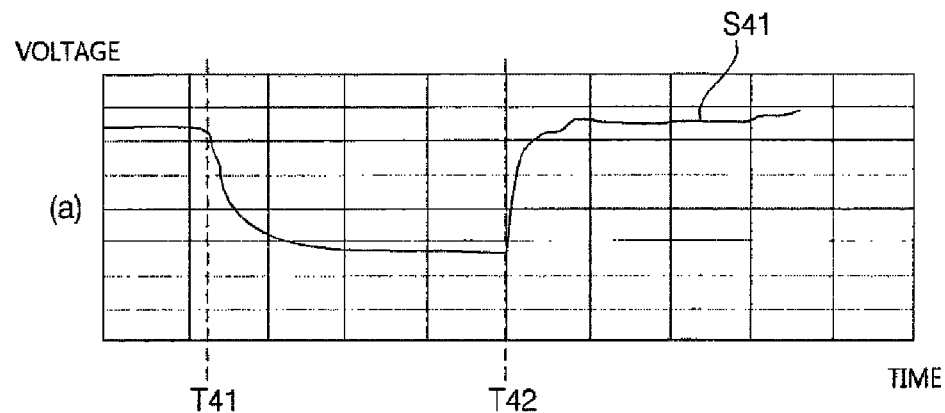
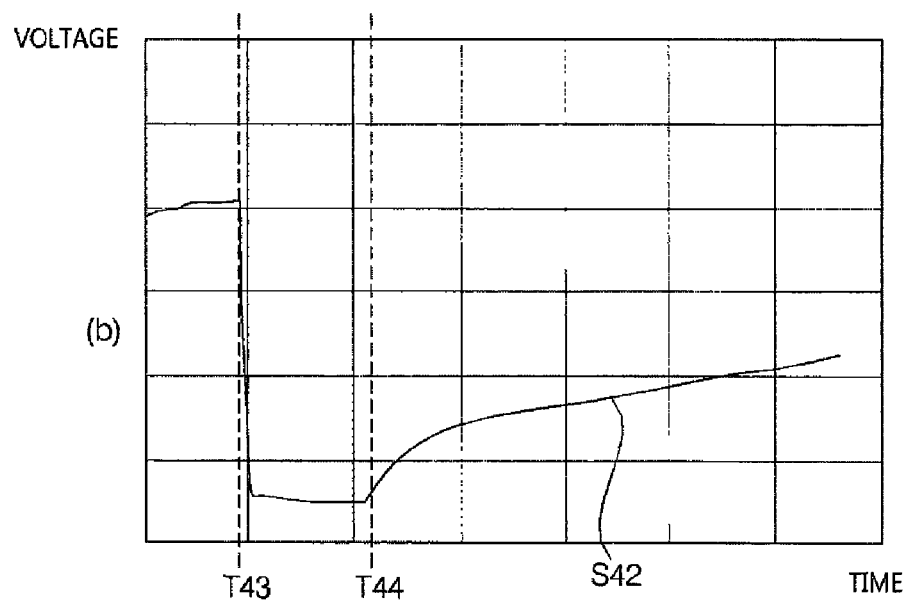

[Fig. 7]
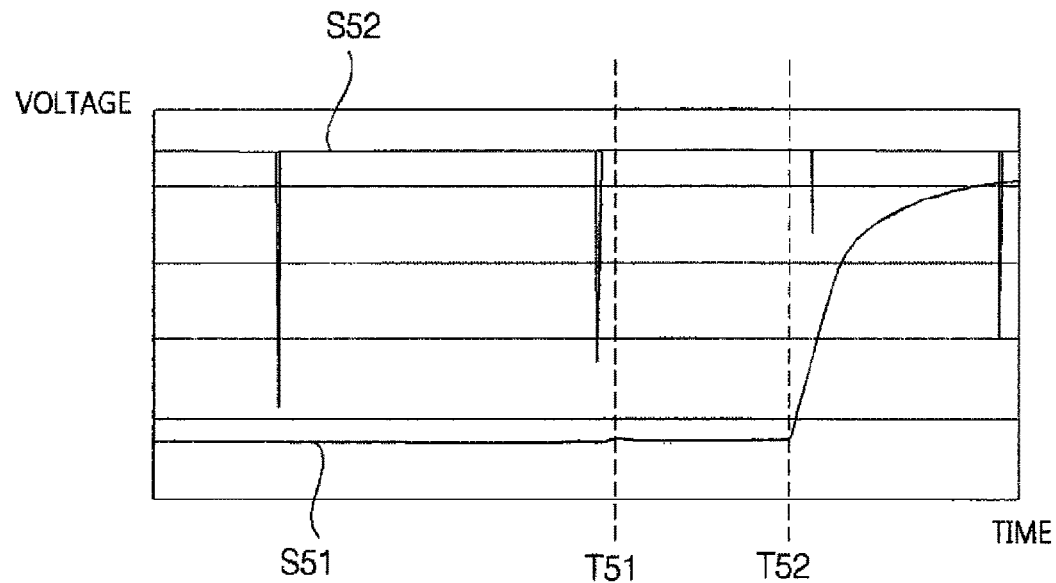
[Fig. 8]
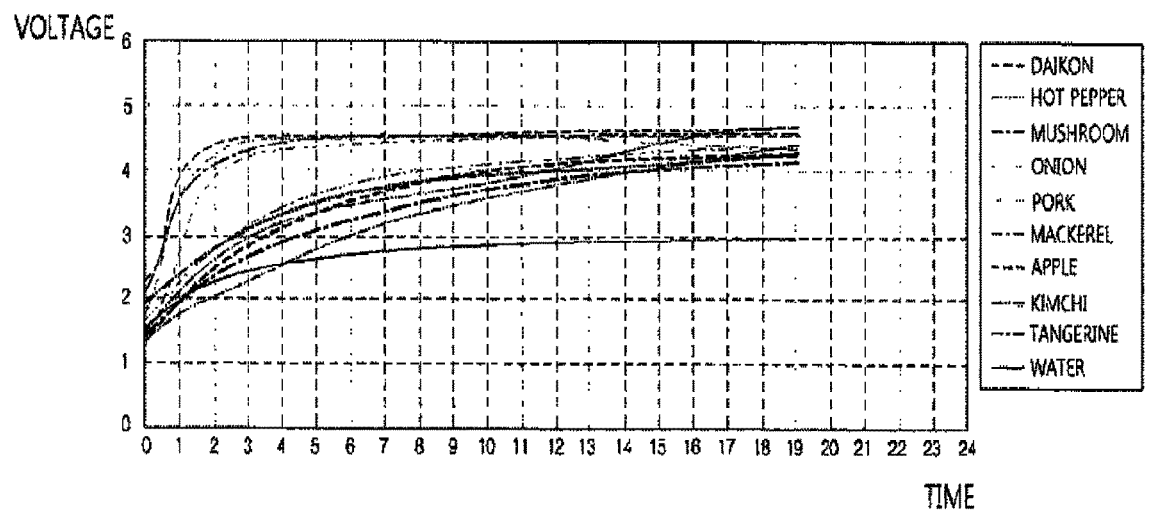

[Fig. 9]
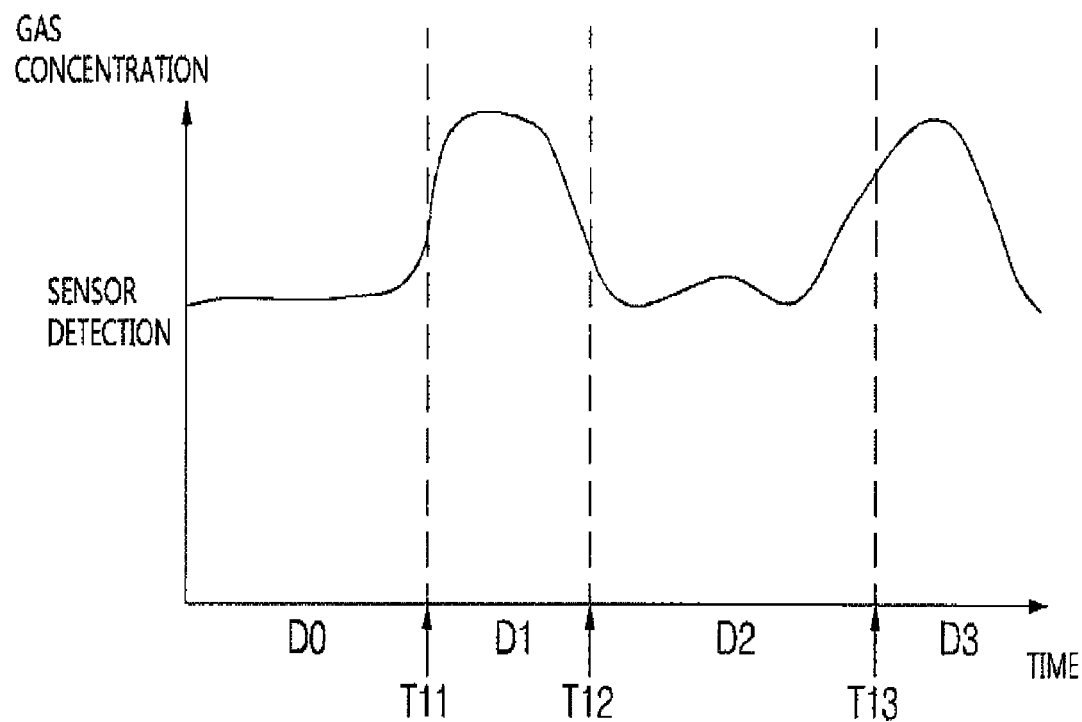

[Fig. 10]
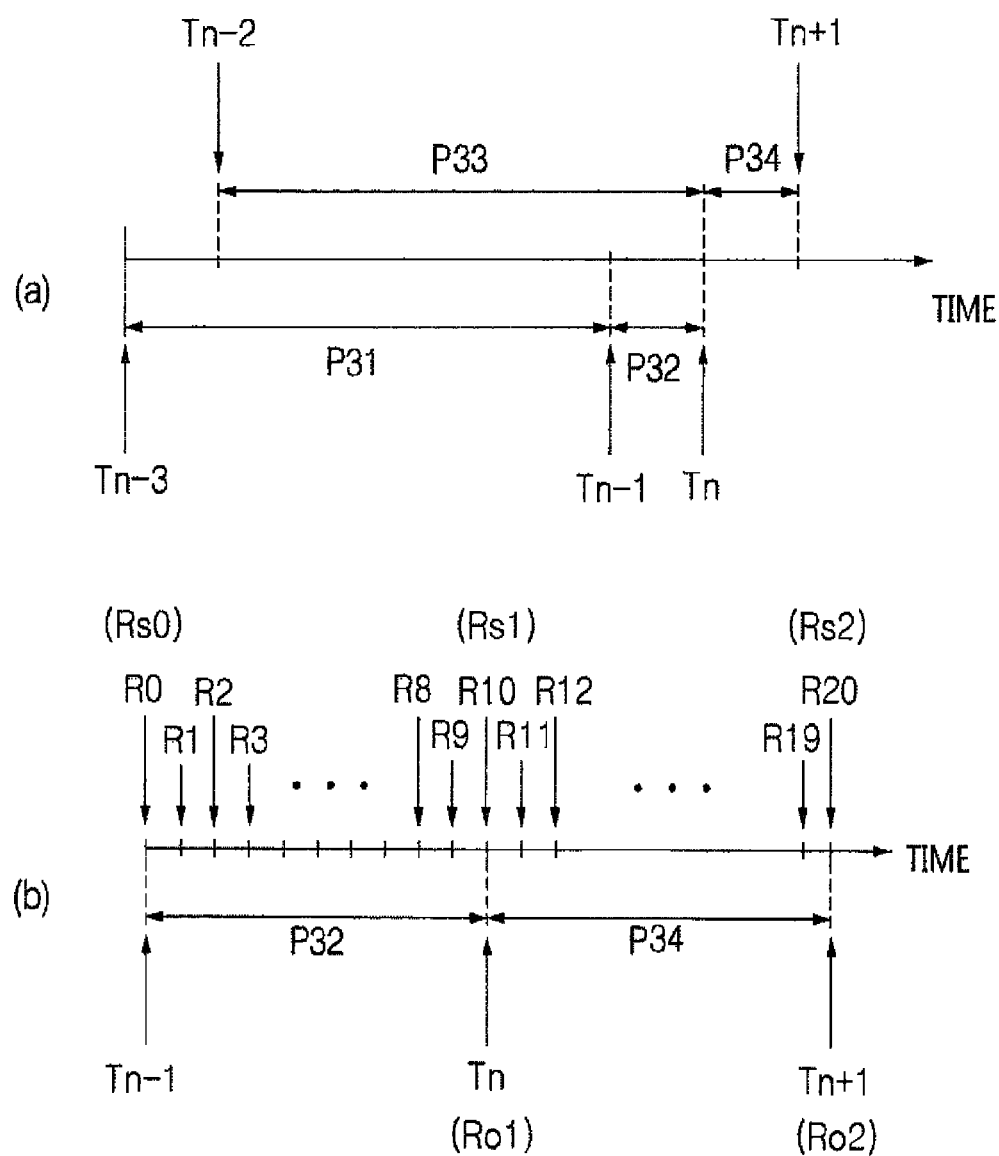

[Fig. 11]
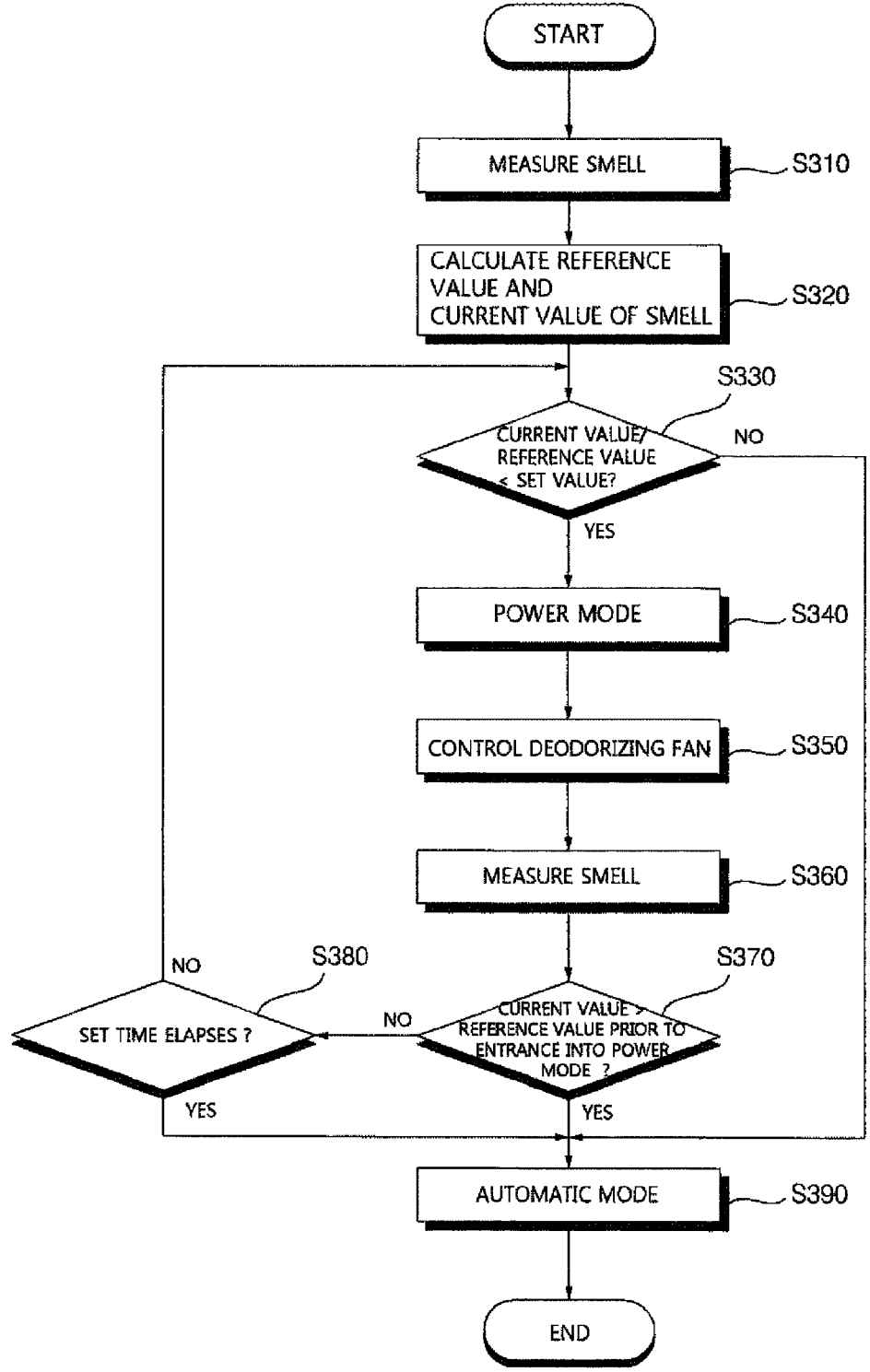

[Fig. 12]
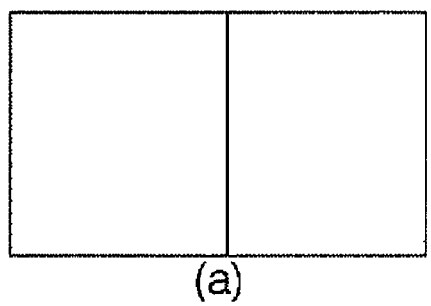
(a)
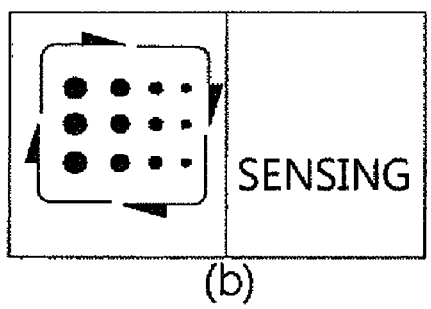
(b)
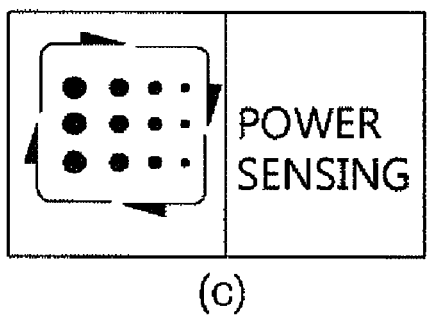
(c)

REFRIGERATOR AND METHOD OF CHANGING A DEODORIZING MODE ACCORDING TO A DETECTED SMELL

CROSS-REFERENCE TO RELATED PATENT APPLICATIONS

This application is a U.S. National Stage Application under 35 U.S.C. § 371 of PCT Application No. PCT/KR2016/010391, filed Sep. 16, 2016, which claims priority to Korean Patent Application No. 10-2015-0131229, filed Sep. 16, 2015, whose entire disclosures are hereby incorporated by reference.

TECHNICAL FIELD

The present invention relates to a refrigerator and a control method thereof, and more particularly to, a refrigerator and a control method thereof, for deodorization of food in the refrigerator.

BACKGROUND ART

A refrigerator is a device for providing chilled air thereinto and includes a refrigerant circulation system.

In general, the refrigerant circulation system includes a compressor for compressing a refrigerant, a condenser through which a high-temperature and high-pressure refrigerant discharged from the compressor flows, an extension valve for expanding the refrigerant passing through the condenser at low temperature and low pressure, and an evaporator through which the refrigerant passing through the extension valve flows and exchanges heat with external air.

Air cooled by exchanging heat with the evaporator flows into a cooler. The compressor and the condenser are installed in a machine chamber provided at a rear side of the refrigerator. In the case of a cooling device, in order to exchange heat between the condenser and indoor air, a fan is installed at one side of the condenser. Accordingly, indoor air blown by the indoor fan contacts the condenser and exchanges heat.

A refrigerator provides different chilled air to inner spaces of a plurality of chambers of the refrigerator so as to store foodstuffs with different storage conditions in the respective chambers.

Since a refrigerator stores foodstuffs, foodstuffs may generate smells in the refrigerator and may affect other stored foods.

Accordingly, a refrigerator has a deodorizing function so as to deodorize foodstuffs in the refrigerator.

However, foodstuffs continuously generate smells, and in particular, whenever a new foodstuff is put in a refrigerator, new smell corresponding thereto is generated and, thus, it is not easy to deodorize the refrigerator.

Thus, a user may use a deodorizing aid but the deodorizing aid needs to be periodically exchanged due to a limited lifetime thereof.

Accordingly, there is a need for a method of more effectively deodorizing foodstuffs in a refrigerator.

DISCLOSURE OF INVENTION

Technical Problem

Therefore, the present invention has been made in view of the above problems, and it is an object of the present invention to provide a refrigerator and a method of controlling the same, for detecting smell generated from a food to remove the smell during containing foodstuffs.

Solution to Problem

In accordance with an aspect of the present invention, the above and other objects can be accomplished by the provision of a refrigerator including a smell sensor for detecting smell in the refrigerator, a deodorizer for adsorbing, sterilizing, and deodorizing air in the refrigerator, and a controller for calculating detected values of detected signals detected by the smell sensor, changing a deodorizing mode according to the detected smell, and controlling the deodorizer, wherein, upon determining that intensity of the smell is increased, the controller changes the deodorizing mode to a power mode from a normal automatic mode and controls the deodorizer to repeatedly operate for a set time period so as to remove smell in the refrigerator.

The controller may calculate an average of the detected values according to a cooling cycle of the refrigerator and determine change in smell.

The smell sensor may be a semiconductor-type gas sensor. In addition, the smell sensor may include any one of $In_2O_2$ and $SnO_2$ that react with $H_2S$, TMA, and MM that are smells of foodstuffs as a detection material.

The smell sensor may include a device heater for heating the detection material at a heating temperature that is equal to or less than an ignition point of refrigerant gas in the refrigerator, 325° C.

In accordance with another aspect of the present invention, there is provided a method of controlling a refrigerator, the method including detecting smell in the refrigerator by a smell sensor, changing a deodorizing mode to a power mode from a normal automatic mode when determining change in smell in the refrigerator according to detected signals of the smell sensor and determining that smell intensity is increased, repeatedly operating a deodorizer for a set time period to sterilize and deodorize air in the refrigerator according to the power mode, re-detecting smell through the smell sensor during an operation in the power mode, and releasing the power mode and resetting the normal automatic mode when smell intensity is reduced compared with a case before the power mode is set.

Advantageous Effects of Invention

The refrigerator and the method of controlling the same according to the present invention may detect smell and control a deodorizing function according to the smell to effectively use a filter in order to remove unpleasant smell in the refrigerator due to smell generated from a foodstuff, and may rapidly remove smell even when a foodstuff is input to generate smell so as to reduce user displeasure and to prevent the smell from affecting other foodstuffs, thereby enhancing convenience.

BRIEF DESCRIPTION OF DRAWINGS

The above and other objects, features and other advantages of the present invention will be more clearly understood from the following detailed description taken in conjunction with the accompanying drawings, in which:

FIG. 1 is a diagram illustrating a refrigerator according to an exemplary embodiment of the present invention;

FIG. 2 is a schematic block diagram illustrating main components of a refrigerator according to an exemplary embodiment of the present invention;

FIG. 3 is an exploded perspective view illustrating components of a deodorizer of a refrigerator according to an exemplary embodiment of the present invention;

FIG. 4 is a diagram for explanation of a position of a sensor for detecting smell of a refrigerator according to an exemplary embodiment of the present invention;

FIG. 5 is a diagram illustrating components of a smell sensor according to an exemplary embodiment of the present invention;

FIG. 6 is a graph illustrating sensor properties according to a type of a waterproofing material of a smell sensor, according to an exemplary embodiment of the present invention;

FIG. 7 is a graph illustrating a detected signal according to a type of a smell sensor according to an exemplary embodiment of the present invention;

FIG. 8 is a graph illustrating change in a detected signal of a food type in a refrigerator according to an embodiment of the present invention;

FIG. 9 is a diagram illustrating change in smell according to setting of a deodorizing mode of a refrigerator according to an embodiment of the present invention;

FIG. 10 is a diagram for explanation of a method of detecting and removing smell in a refrigerator according to an embodiment of the present invention;

FIG. 11 is a flowchart illustrating a control method for deodorization of a refrigerator according to an exemplary embodiment of the present invention; and FIG. 12 is a diagram illustrating an example of a display unit of a refrigerator according to an exemplary embodiment of the present invention.

BEST MODE FOR CARRYING OUT THE INVENTION

Hereinafter, the present invention will be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. The same reference numerals in the drawings denote like elements.

FIG. 1 is a diagram illustrating a refrigerator 1 according to an exemplary embodiment of the present invention.

As illustrated in FIG. 1, an outer appearance of the refrigerator 1 according to the present invention may be formed by a case 11 for forming inner spaces divided by a refrigerating chamber 12 and a freezing chamber 13, refrigerating chamber doors 14 and 15 for opening and closing the refrigerating chamber 12, and a freezing chamber door.

The refrigerating chamber 12 may be opened and closed by the refrigerating chamber doors 14 and 15 that are disposed at left and right sides thereof, respectively.

The refrigerating chamber doors 14 and 15 may include the left refrigerating chamber door 14 that is rotatably connected to a left side of the case 11 and the right refrigerating chamber door 15 that is rotatably connected to a right side of the case 11.

In this case, the refrigerating chamber 12 may be opened by a left door and a right door to constitute one chamber but, as necessary, left and right separate seals may be included. A door of a refrigerating chamber may be rotatably connected to a case.

A hinge portion may allow the refrigerating chamber doors 14 and 15 to be rotatably connected to the case 11. The hinge portion may include a hinge portion for connecting the left refrigerating chamber door 14 to the case 11 and a hinge portion for connecting the right refrigerating chamber door 15 to the case 11. The hinge portion to which the left refrigerating chamber door 14 is connected may have the same structure as the hinge portion to which the right refrigerating chamber door 15 is connected.

The hinge portion may include a door switch (not shown) and, thus, the door switch is switched on or off during opening or closing of the right refrigerating chamber door 15 so as to turn on/off a light for illuminating the refrigerating chamber 12. The door switch may turn off the light during closing of the right refrigerating chamber door 15 and turn on the light during opening of the right refrigerating chamber door 15.

The door switch may further include a door switch connector (not shown) and, as the door switch connector is retracted inward, whether a refrigerator is opened or closed may be detected.

The freezing chamber 13 may include doors that are opened and closed in right and left directions.

As necessary, the freezing chamber 13 may be slidably coupled along the case 11 and may accommodate foodstuffs. In this case, the freezing chamber door may slide toward an inner side of the case 11, seal the freezing chamber 13 during accommodation of foodstuffs, and open the freezing chamber 13 when the freezing chamber door is pulled and protrudes from the case 11. As such, the refrigerator may further include a separate sliding storage chamber.

A door of the refrigerating chamber 12 may include a control panel (not shown). The control panel may include an input unit (not shown) including at least one button for setting driving of the refrigerator 1 and a display unit (not shown) for displaying a current driving mode and driving state of the refrigerator.

The refrigerating chamber 12 may include a deodorizer 16 installed therein. The deodorizer 16 may include a smell sensor (not shown) disposed in a panel 17 so as to measure intensity of smell inside the refrigerating chamber 12. In this case, the panel 17 may include a light.

The deodorizer 16 may be operated in a set deodorizing mode to circulate air inside the refrigerating chamber 12. In this case, the deodorizer 16 may absorb air in the refrigerating chamber and blow the absorbed air through an included filter so as to allow impurities, smells, germs, and so on to be absorbed by the filter. Accordingly, the deodorizer 16 may sterilize air in the refrigerator and remove smells. The deodorizer 16 may be changed to a deodorizing mode from an operation mode in response to intensity of smell, measured by the smell sensor, and may be operated according to the set deodorizing mode.

The input unit may be embodied as a mechanical button or a capacitive/static pressure type of touch button, for receiving various operation commands from a user. In this case, the input unit may include a mode selector for setting a kimchi mode.

The display unit may visualize and display state information or malfunction information of the refrigerator 1 using a luminous body such as a light emitting diode (LED), a liquid crystal display (LCD), and an organic electroluminescent (EL) display. In addition, a control panel may include a lamp (not shown) that is turned on and off so as to display a state of the refrigerator 1 and include a sound output unit for outputting sound of a buzzer, a speaker, or the like.

The refrigerator 1 may perform refrigerating or freezing while a refrigerant is circulated along a refrigerant pipe with a circulation cycle of compression, expansion, evaporation, and condensation and exchanges heat with surrounding air via phase transition of the refrigerant during a procedure of the circulation cycle. To this end, the refrigerator 1 may include a compressor (not shown) for compressing a refrigerant, an expansion valve (not shown) for expanding the refrigerant, a heat exchanger (not shown) that functions as an evaporator for evaporating the refrigerant, a heat exchanger (not shown) that functions as a condenser for condensing the refrigerant, a fan (not shown) for blowing heat-exchanged air, a refrigerating chamber fan, and a freezing chamber fan. The refrigerator 1 may include a plurality of sensors.

The refrigerator 1 may control a cooling system based on a set driving mode and a measured temperature to form an environment for preserving foodstuffs accommodated in each chamber.

FIG. 2 is a schematic block diagram illustrating main components of the refrigerator 1 according to an exemplary embodiment of the present invention.

As illustrated in FIG. 2, the refrigerator 1 includes an input unit 170, a display unit 180, a detector 120, a data unit 190, a compressor 161, a freezing chamber fan 141, a refrigerating chamber fan 151, a freezing chamber fan driver 140, a refrigerating chamber fan driver 150, a compressor driver 160, a deodorizer 130 or 16, and a controller 110 for controlling an overall operation of the refrigerator 1.

The detector 120 may include a plurality of sensors, detect an operating state of the refrigerator 1, and input the resulting information to the controller 110. The detector 120 may include a plurality of sensors such as a temperature sensor 121, a pressure sensor, a smell sensor 122, a fan motor sensor, and a defrosting sensor, which will be described below.

The temperature sensor 121 may include a refrigerating temperature sensor for detection of a temperature of the refrigerating chamber 12, a freezing chamber temperature sensor for detecting a temperature of the freezing chamber 13, an outdoor temperature sensor for measuring a temperature of an indoor space, and a temperature sensor for detecting a temperature of a refrigerant.

The smell sensor 122 may detect smell in the refrigerating chamber 12. The smell sensor 122 may be included in a freezing chamber as well as in a refrigerating chamber. In this case, the smell sensor 122 may be a gas sensor that detects smell generated from foodstuffs in the refrigerating chamber.

The deodorizer 130 or 16 may include a deodorizing fan 131, a filter 132, and a sterilizing lamp 133.

The deodorizing fan 131 may circulate air in the refrigerator and, in particular, may absorb air in the refrigerating chamber and blow the absorbed air through a filter and to re-circulate in the refrigerating chamber. In this case, the deodorizing fan 131 may externally blow the air in the refrigerator as necessary.

In addition, when the smell sensor 122 detects smell in the refrigerator and intensity of smell is a predetermined value or more, the deodorizing fan 131 may be operated according to a control command of the controller 110 to discharge air inside the refrigerator so as to deodorize the refrigerator.

A sterilizing lamp 133 is turned on for a predetermined time so as to remove viruses or germs. In this case, the sterilizing lamp 133 may include a visible-light emitting diode (LED) and may emit light to the filter 132 so as to enhance sterilizing power of the filter.

The filter 132 may include a plurality of filters and adsorb, filter, and remove floating matter, e.g., powdery dust or viruses in the refrigerating chamber 12. In this case, when a sterilizing lamp 133 is turned on, sterilizing power of the filter 132 may be enhanced by light of the sterilizing lamp. The filter 132 may have a deodorizing effect of adsorbing smell particles and removing smell.

The data unit 190 may store control data of a refrigerator for control of an operation of the refrigerator 1, data on input driving setting, reference data for determining whether the refrigerator is normally operated, and driving data measured or generated during an operation of the refrigerator.

The data unit 190 may store measurement data measured and input from the detector 120. In particular, the data unit 190 may accumulate and store smell data measured by the smell sensor 122 and store data for determination of intensity of smell.

The input unit 170 may be included in the aforementioned control panel and may input data on a driving mode or driving setting of the refrigerator 1. The input unit 170 may include at least one button or touch input element. For example, the input unit 170 may include a lock button for a key-lock function, a temperature setting button for temperature setting for each chamber, and a driving mode button so as to restrict user input.

The display unit 180 may be included in the control panel and may display a driving state and operating state of the refrigerator 1 via a combination of an image, a number, a special character, and so on.

The display unit 180 may display a temperature and operating state of each chamber, i.e., a refrigerating chamber and a freezing chamber and, in particular, may display information on intensity of smell of the refrigerating chamber or the freezing chamber or information on a deodorizing mode for deodorization.

The refrigerator 1 may further include a speaker for outputting warning or effect sounds according to an operation and a lamp for indicating an operating state via whether the lamp is turned on or off, lamp lighting color, and lighting control in addition to the display unit 180.

The controller 110 may set an operation of the refrigerator 1 in response to data input from the input unit 170 and output an operating state through the display unit 180. The controller 110 may output a state of each chamber of a refrigerator through the display unit 180 and may differently control chambers in response to data input through the input unit 170. In addition, the controller 110 may analyze and control a driving state of the refrigerator 1 based on information collected through various sensors included in the detector 120.

The controller 110 may determine intensity of smell in response to smell data input from the smell sensor 122 and accumulate and store smell data in the data unit 190.

The controller 110 may receive smell data from the smell sensor 122 at a predetermined time interval and determine intensity of smell at a predetermined time interval. The controller 110 may control the deodorizer 130 to deodorize foodstuffs in the refrigerator in response to intensity of smell.

The controller 110 may calculate an average of smell based on data accumulated to determine intensity of smell and determine the intensity of smell. As described above, since the refrigerator 1 is configured to supply chilled air according to refrigerant circulation, a detected value of a smell sensor may also be changed according to change in the air current and temperature at a time point of inputting chilled air according to a refrigerating/cooling cycle and, thus, an average of detected values of measured smell.

In order to set a deodorizing mode, the controller 110 may compare smell intensity before the deodorizing mode is changed and smell intensity after predetermined time elapses since the deodorizing mode is changed based on a time point when the deodorizing mode is changed and reset the deodorizing mode.

The controller 110 may set the deodorizing mode to a normal automatic mode or a power mode and control the deodorizer 130 in response to the smell intensity. In this case, the display unit 180 may display the normal automatic mode or the power mode in response to the deodorizing mode set by the controller 110.

The controller 110 may control rotation speed and operation time of the deodorizing fan 131 according to a deodorizing mode and operate the deodorizer 130 at a predetermined period in response to the set deodorizing mode to blow air in the refrigerator through the filter 132 and the sterilizing lamp 133 so as to remove smell.

For example, in the normal automatic mode, the deodorizer 130 may be on standby during 60 minutes after an operation during 10 minutes and may repeatedly perform this operation at a period of 70 minutes. In the power mode, the deodorizer 130 may repeatedly perform an operation at a period of 15 minutes so as to operate during 10 minutes and then to stop for 5 minutes.

In particular, after predetermined time elapses since foodstuffs are input, as smell intensity is strengthened, the controller 110 may detect smell through the smell sensor 122 and set a deodorizing mode so as to immediately perform deodorization after foodstuffs are input.

When the smell sensor 122 malfunctions, the controller 110 may change the power mode to the normal automatic mode. When the smell sensor malfunctions, if a door is opened using a door switch, the controller 110 may set the power mode based on a time point at which the door opened. That is, assuming that foodstuffs are input at a time point at which a door is opened, the controller 110 may control the deodorizer 130 to operate in the power mode for a predetermined time period so as to remove smell after the door is opened.

The compressor driver 160 may supply operation power so as to operate the compressor 161 in response to a control command of the controller 110 and control driving of the compressor 161. In this case, the compressor driver 160 may include an inverter (not shown) and an inverter driver (not shown), for control of the compressor 161.

The refrigerating chamber fan driver 150 may control rotation operation and rotation speed of the refrigerating chamber fan 151 so as to supply heat-exchanged chilled air to the refrigerating chamber 12. In addition, the freezing chamber fan driver 140 may control rotation operation and rotation speed of the freezing chamber fan 141 so as to supply heat-exchanged chilled air to the freezing chamber 13.

The compressor 161 may compress a refrigerant to circulate in the refrigerator 1 and adjust the refrigerant to temperature of discharged chilled air. The refrigerating chamber fan 151 and the freezing chamber fan 141 may blow chilled air that exchanges heat with the refrigerant by a heat exchanger into the refrigerating chamber and the freezing chamber.

FIG. 3 is an exploded perspective view illustrating components of a deodorizer of a refrigerator according to an exemplary embodiment of the present invention.

As described above, the deodorizer 130 may include the deodorizing fan 131, the filter 132, and the sterilizing lamp 133.

As illustrated in FIG. 3, the deodorizer 130 or 16 may be included in the panel 17 installed in an internal wall of the refrigerating chamber 12. The panel 17 may be installed in the internal wall of the refrigerating chamber 12 and may include a refrigerating chamber light installed therein. The panel 17 may include the smell sensor 122 installed therein.

The deodorizer 16 or 130 may include the deodorizing fan 131, a fan case 135, a sterilizing lamp module 133a, a filter case 134, a plurality of filters 132, a deodorizer case 136, a connection plate 137, and a deodorizer front case 138.

The deodorizing fan 131 may be inserted into the panel 17 and the fan case 135 may support the deodorizing fan 131 so as to fix the deodorizing fan 131 to the panel 17. The sterilizing lamp module 133a may include the sterilizing lamp 133 inserted thereinto. In this case, the sterilizing lamp 133 may include at least one visible ray LED. The deodorizer case 136 may be connected to the fan case 135 and may cover the filter case 134 from the sterilizing lamp module 133a. The connection plate 137 may connect the deodorizer case 136 and the deodorizer front case 138 and form a space so as to blow air between the deodorizer case 136 and the deodorizer front case 138.

The filter 132 may be inserted into the filter case 134. The filter 132 may include a first photocatalyst filter 132a, a first deodorizing filter 132b, a second deodorizing filter 132c, and a second photocatalyst filter 132d. That is, the filter 132 may include the two photocatalyst filters 132a and 132d and the two deodorizing filters 132b and 132c. In this case, configuration of a filter may be varied.

In this case, the filter 132 may be divided into a front filter for primarily filtering floating matter (viruses and dust) in the air in the refrigerating chamber and a filter for absorbing minute particles and viruses through a filter with air permeability and dense pores.

The photocatalyst filters 132a and 132d may each be a filter coated with a photocatalyst, may be disposed to directly face each other so as to receive a large amount of light from the sterilizing lamp 133, and may have sterilizing power that is enhanced as a portion of the filter 132, to which light is emitted, is widened.

Accordingly, the deodorizer case 136 and the filter case 134 may form a space such that the sterilizing lamp module 133a and the filter 132 are spaced apart from each other by a predetermined interval so as to emit light of the sterilizing lamp 133 to the filter 132. In this case, the filter 132 and the sterilizing lamp 133 may be inclined 20 to 45° C. to the horizontal direction. As a portion of the filter 132, to which light is emitted, is increased, an effect of the photocatalyst may be maximized and, thus, the sterilizing lamp 133 may use a chip type LED.

As a distance between the filter 132 and the sterilizing lamp 133 is increased, an emissive range is widened but light intensity is weakened and, thus, a distance between the filter 132 and the sterilizing lamp 133 may be set to 3 to 10 mm. In this case, the sterilizing lamp module 133a may be coated with silicon in order to prevent the sterilizing lamp 133 from being damaged by water.

In this case, the photocatalyst filter may generate electrons (e−) and holes (h+, particles that show the same behavior as electrons with + electric charges) via reaction between emitted light and the photocatalyst coated on a surface of the photocatalyst filter, electrons may react with oxide of a photocatalyst surface to generate superoxide, and holes may react with moisture present in the air to generate hydroxyl radicals (OH—).

Since the generated hydroxyl radicals have excellent capability of oxidation-decomposing highly organic materials, hydroxyl radicals may decompose malodorous substances, virus, and germs such as bacteria, which are always present in the air to be changed to water (H2O) and carbon dioxide (CO2).

The photocatalyst reaction corresponds to a competing reaction between recombination of electrons and holes and oxidation and reduction reactions, and as a time period in which electrons and holes are generated and maintained is increased, oxidation and reduction reactions are more advantageous and, thus, when metal such as Cu is used together, recombination may be delayed to enhance a photocatalyst effect.

The photocatalyst has sterilizing and deodorizing effects and, thus, the photocatalyst filters 132a and 132d may have a deodorizing effect as well as a sterilizing effect.

Although the photocatalyst filters 132a and 132d have a deodorizing effect, speed of removing and dissolving smell is low and, thus, the filter 132 may include a separate filter, that is, the deodorizing filters 132b and 132c.

The deodorizing filters 132b and 132c may easily absorb and remove smells using activated carbon. The deodorizer 130 includes two deodorizing filters 132b and 132c and also includes a photocatalyst filter with a deodorizing effect so as to rapidly remove smells.

In this case, the deodorizing filters 132b and 132c are disposed between the first photocatalyst filter 132a and the second photocatalyst filter 132d and, thus, light of the sterilizing lamp 133 is emitted to the photocatalyst filter so as to primarily sterilize room air and to remove smells via a deodorizing filter. The deodorizing filter may be a mesh type filter with large pores.

Accordingly, air passing through the deodorizer 130 may be sterilized and may also be deodorized.

In this case, light of the sterilizing lamp 133 may also be reflected and emitted to the second photocatalyst filter 132d that is a front filter that is farthest from the sterilizing lamp 133. Since the deodorizing filter is of a mesh type, light of the sterilizing lamp 133 may also be emitted to the second photocatalyst filter through the deodorizing filter. The first photocatalyst filter may also be formed of a material through which light is capable of passing, for example, felt.

FIG. 4 is a diagram for explanation of a position of a sensor for detecting smell of a refrigerator according to an exemplary embodiment of the present invention.

The smell sensor 122 may be installed in the panel 17 including the deodorizer 130 or 16.

In this case, the smell sensor 122 is not capable of detecting smell when smell is removed by the deodorizer 130 and, thus, the smell sensor 122 may be installed around the deodorizer 130 or 16 so as to detect smell of air that is not sterilized and deodorized by the deodorizer 130.

In the case of a windy place, gas (smell particles) unstably flows due to air flow and, thus, there may be a deviation in detection capability of the smell sensor 122. Accordingly, the smell sensor 122 may be installed at a position that is spaced apart from a discharge port of the refrigerating chamber fan 151, is around the deodorizer 130, and is barely affected by air flow of the deodorizer 130.

Accordingly, the smell sensor 122 may be installed at any one of an upper side P3, a lower side P2, a left side P1, and a right side P4 except for a portion that perpendicularly meets wind of a deodorizing fan based on the deodorizer 130 or 16 so as to measure smell in the air inside the refrigerating chamber.

FIG. 5 is a diagram illustrating components of the smell sensor 122 according to an exemplary embodiment of the present invention.

As illustrated in FIG. 5(a), the smell sensor 122 may include a sensor module 210, a case 220, a connector 221, and a signal line 222.

In this case, the sensor module 210 may be fixedly installed in a sensor board 224 and the sensor board 224 may include a processing circuit for processing a signal of the sensor module 210 and transmitting the signal to the connector 221.

A waterproofing material 223 may be molded to waterproof an inner side of the case 220 while the sensor module 210, the connector 221, and the signal line 222 are completely installed.

In this case, the waterproofing material 223 may protect processing circuits installed in the sensor module 210 and the sensor board 224 and the connector 221 for signal transmission from moisture, and the sensor board 224, the sensor module 210, and the connector 221 may be partially molding-processed by the waterproofing material 223. The waterproofing material 223 may be higher than at least the sensor board 224 and lower than an upper end of the sensor module 210. This is because, when the waterproofing material 223 is molding-processed to be higher than the upper end of the sensor module 210, smell particles may not reach an inner side of the sensor module 210 and, thus, it is not possible to detect smell. The waterproofing material 223 may be urethane. When silicon is used as the waterproofing material 223, performance of the sensor module 210 may be affected and, thus, urethane molding may be used.

As illustrated in FIGS. 5(b) and 5(c), the sensor module 210 may include a sensor cap 211 for protecting sensors therein and bridges 212 for fixedly installing the sensor module 210 to the sensor board 224 and applying detected signals to the sensor board 224. Accordingly, the signals detected by the sensor module 210 may be applied to the sensor board 224 through the bridges 212, applied to the connector 221 from a processing circuit in the sensor board 224, and transmitted to the controller 110 through the signal line 222.

Although the sensor cap 211 is illustrated as being cylindrical, a shape of the sensor cap 211 is not limited to the cylindrical shape and, thus, may have a rectangular shape and any shape as long as sensors are protected from external shock.

At least one hole 213 may be formed in an upper portion of the sensor cap 211. For example, four holes may be formed. The holes 213 of the sensor cap 211 may be formed with a size for allowing smell particles to pass therethrough to reach the sensors in the sensor cap 211. As necessary, an upper side of the sensor cap 211 may be formed as a mesh.

In this case, the sensor cap 211 may be a metallic material and moisture may be formed on a surface of the sensor cap 211 due to low temperature of an inner part of the refrigerator 1. However, since a portion of the sensor module 210 is molding-processed by the waterproofing material 223, even if water on the surface of the sensor cap 211 flows down, an operation of the sensor module 210 is not affected.

The formed moisture may clog the holes 213 or penetrate into a sensor through the holes 213. However, the sensor includes a device heater 204 to be described below so as to emit heat and, thus, heated air in the sensor cap 211 may be moved upward and externally discharged through the holes 213, thereby preventing the holes 213 from being clogged by moisture or preventing moisture from penetrating the sensor through the holes 213.

The sensor will be described in terms of a semiconductor-type gas sensor as an example. The semiconductor-type gas sensor may be manufactured with a small size, may also be operated at a low temperature, may be driven using a simple method, and may be easily applied to a refrigerator for containing foodstuffs due to non-toxicity thereof. Since a refrigerant flows in a refrigerator, a semiconductor-type gas sensor having a sensor device heater, a threshold temperature of which does not exceed a predetermined temperature, may be used in the case of leakage of refrigerant gas.

The sensor may include the device heater 204, a substrate 203, electrodes 202, and a detection material 201.

The detection material 201 may react with particles in the air to generate a predetermined signal and may be an n-type oxide semiconductor-based detection material.

Various metallic oxides may be used as the detection material 201 according to gas to be detected. For example, the detection material 201 may be $SnO_2$, $ZnO$, $WO_4$, $Fe_2O_3$, or $In_2O_3$. In this case, the smell sensor 122 may be installed in the refrigerator in order to detect smell of foodstuffs and may be formed of a detection material that reacts with smell of foodstuffs among the aforementioned metallic oxides. Smell of foodstuffs may mainly correspond to H2S, TMA, or MM and, thus, the detection material may be $In_2O_2$ or $SnO_2$ which reacts with these gas components.

The device heater 204 may heat the substrate 203 to cause reaction of the detection material 201. Hereinafter, the substrate 203 may be formed of, for example, aluminum and the device heater 204 may be formed of, for example, ruthenium oxide ($RuO_2$).

An interaction of the detection material 201 with gas-phase molecules may become active at a high temperature and may also proceed in a semiconductor and, thus a defect concentration of oxide may be affected to change conductivity. Accordingly, the device heater 204 may heat the substrate 203 to enhance reactivity of the detection material 201.

Since the smell sensor 122 continuously operates, the device heater 204 of a sensor emits heat for a long time and, thus, a threshold temperature of the device heater 204 may not exceed a predetermined temperature. In particular, since a refrigerant flows in the refrigerator 1, when refrigerant gas leaks, there is a possibility of the refrigerant gas being ignited by the device heater 204 of the smell sensor 122 and, thus, a sensor with a low threshold temperature of the device heater 204 may be used for safety. For example, a sensor of the device heater 204 with a threshold temperature 325° C. or less may be used.

The device heater 204 is a component that emits heat and has opposite property to that of the refrigerator 1 that supplies chilled air so to contain foodstuffs. As described above, air that is heated in the sensor cap 211 by the device heater 204 may be externally discharged through the holes 213. However, even if the device heater 204 emits heat and a temperature of the device heater 204 is high, temperature change by the device heater 204 is low at a portion spaced apart the sensor module 210 by a predetermined distance and, thus, the device heater 204 may not affect an internal temperature of the refrigerator 1.

For example, when the device heater 204 emits heat to increase a temperature to 200° C. or more, a measured temperature of the sensor cap 211 for protecting sensors is about 16 to 18° C., a measured temperature of a portion that is spaced apart from the sensor module 210 by 5 mm is about 1.7 to 2.3° C., and a measured temperature of a portion spaced apart from the sensor module 210 by 2 cm is about 0 to 0.1° C. The sensor cap 211 are provided around the sensor including the device heater 204, the case 220 is installed outside the sensor cap 211, a portion spaced apart from the sensor module 210 by 5 mm is an inner portion of the case 220, and a measured temperature of a portion spaced apart from the sensor module 210 by 2 cm is low, as described above and, thus, the device heater 204 may not affect temperature change around the smell sensor 122.

With regard to the smell sensor 122 configured as such, when the detection material 201 reacts with materials in the air, as electrical conductivity between the electrodes 202 is changed, the smell sensor 122 may output a signal corresponding thereto so as to detect smell.

The smell sensor 122 may be configured in such a way that free electrons between the electrodes 202 are combined with oxygen having high electron affinity in the air and the number of free electrons is reduced to lower electrical conductivity and to correspondingly enhance resistance, in fresh air.

In polluted air, that is, when reducing gas is present, reducing gas is combined with oxygen and oxygen gas on a surface of the detection material 201 is reduced and, thus, the number of free electrons is increased, enhancing electrical conductivity and reducing resistance.

Accordingly, in polluted air, the smell sensor 122 may have increased electrical conductivity and reduced resistance and, thus, may output a predetermined signal corresponding thereto so as to detect smell.

FIG. 6 is a graph illustrating sensor properties according to a type of a waterproofing material of a smell sensor, according to an exemplary embodiment of the present invention.

The refrigerator 1 may be configured to supply chilled air to maintain a predetermined temperature and, thus, the smell sensor 122 may be waterproofed in order to protect an internal electric circuit vulnerable to moisture.

In particular, as described above, the smell sensor 122 may be molding-processed by the waterproofing material 223 in order to protect the sensor module 210, the sensor board 224, and the connector 221, in particular a processing circuit installed in the sensor board 224, installed in the case 220. In this case, the waterproofing material 223 may be urethane.

FIG. 6(a) is a graph illustrating signal change S41 when a smell sensor is exposed to urethane. FIG. 6(b) is a graph illustrating signal change S42 when a smell sensor is exposed to silicon.

As illustrated in FIG. 6(a), when a sensor that is not molding-processed is exposed to urethane at a first time T41, the sensor enters a state in which smell is not detectable and a voltage of an output signal is reduced, but at a second time T42 when a predetermined time period elapses, smell is normally detectable.

As illustrated in FIG. 6(b), when a sensor that is not molding-processed is exposed to silicon at a third time T43, the sensor enters a state in which smell is not detectable and a voltage of an output signal is reduced. At a fourth time T44 when a predetermined time period elapses, it may appear that the sensor operates as a voltage of an output signal of the sensor is increased, but, even if a predetermined time period elapses, the voltage of the output signal does not reach an initial voltage of a detected signal and smell is not normally detected.

When a voltage of a signal before the sensor is exposed to silicon, that is, prior to the third time T43, is a voltage of a normal smell detected signal, a normal smell detected signal may not be output after the sensor is exposed to silicon.

Although silicon is widely used for waterproofing, when the smell sensor is exposed to silicon, it may not be possible to detected smell. Accordingly, the smell sensor 122 may be molding-processed using urethane as the waterproofing material 223.

FIG. 7 is a graph illustrating a detected signal according to a type of a smell sensor according to an exemplary embodiment of the present invention.

A sensor for detection of smell may be a gas sensor or a dust sensor. In order to select a sensor appropriate for smells of foodstuffs among the gas sensor and the dust sensor, kimchi with strong smell may be put in the refrigerator 1 and detected signals may be compared.

As illustrated in FIG. 7, when kimchi is input at a first time T51, a signal of a dust sensor S52 is not changed before and after kimchi is input.

On the other hand, with regard to a gas sensor S51, after a predetermined time period elapses since kimchi is input, a detected signal is changed from a second time T52.

Accordingly, the smell sensor 122 may use a gas sensor for detecting smell of foodstuffs.

FIG. 8 is a graph illustrating change in a detected signal of a food type in a refrigerator according to an embodiment of the present invention.

As illustrated in FIG. 8, when a foodstuff is put in the refrigerator 1, smell is generated from the foodstuff. In this case, the smell sensor 122 may detect smell of the foodstuff to output a signal. A detected value of the smell sensor 122 may be output as a voltage value, and as a voltage value is increased, smell is strengthened.

According a type of a foodstuff, daikon, hot pepper, mushroom, onion, pork, mackerel, apple, kimchi, tangerine, and water are put in the refrigerator 1 and, then, change in smell according to time is detected through the smell sensor 122.

In this case, pork as meat, mackerel as fish, cabbage, onion, daikon, and hot pepper as vegetables, and apple and tangerine as fruits are selected as a variety of foods that are widely consumed. In particular, in the case of vegetables, mushrooms and onions as stem vegetables, hot pepper and apple as fruit vegetables, and daikon and carrot as tubers are selected as commonly purchased vegetables and change in smell thereof is detected. That is, in general, a foodstuff that is frequently put in a refrigerator by a user is selected and change in smells thereof is detected.

H2S is detected from daikon, hot pepper, mushroom, and onion, ammonia and TMA are detected from pork and mackerel, ethylene is detected from apple and tangerine, and MM is detected from kimchi. Accordingly, H2S, TMA, and MM may be set as representative food smells and a gas sensor using, as a detection material, In2O3 or SnO2 that reacts with the food smell may be used as a smell sensor.

In an initial state of inputting a foodstuff, change in a detected signal of the smell sensor 122 is high. According to a type of a foodstuff, smell intensity is largely different but foodstuffs are the same in that change in a detected signal is high in an initial state of inputting a foodstuff.

After a predetermined time period elapses since a foodstuff is input, smell intensity does not increase any longer irrespective of a type of a foodstuff and converges upon a predetermined value.

In the case of kimchi with strong smell, strong smell is measured for a short time but smell intensity is maintained constant after a predetermined time period elapses. In an initial stage in which kimchi, daikon, and mushroom are input, smell intensity is high but, even a food that has originally weak smells is maintained constant with a slight difference after about 18 hours elapses.

Accordingly, the smell sensor 122 may detect smell of various foods and, in particular, detect food smell in an initial state in which a food is input.

In this case, it may be seen that water also has smell but has weak smell compared with other foods. Accordingly, since water has weak smell intensity, water does not affect detection of smell using a smell sensor and change in a deodorizing mode corresponding thereto.

FIG. 9 is a diagram illustrating change in smell according to setting of a deodorizing mode of a refrigerator according to an embodiment of the present invention.

As illustrated in FIG. 9, smell inside the refrigerator 1 may be detected by the smell sensor 122. The smell sensor 122 is a gas sensor and, thus, detects a gas concentration.

In an initial period D0, smell generated from a food that is previously put in the refrigerator 1 is constantly measured by the smell sensor 122. In this case, the deodorizer 130 may operate in a normal automatic mode. In a normal automatic mode, the deodorizer 130 may be on standby during 60 minutes after an operation during about 10 minutes and may repeatedly perform this operation at a period of 70 minutes.

As described above, as time elapses, food smell may have a constant value (concentration), and in the case of the smell sensor 122, when new smell is generated, change in a detected value is high.

When a foodstuff is input at a first time T11, a gas concentration inside a refrigerator is increased due to smell generated from the foodstuff and the smell sensor 122 may detect smell of the newly input foodstuff.

The controller 110 may change a deodorizing mode to a power mode from a normal automatic mode in response to a detected signal of the smell sensor 122. Accordingly, in the first period D1, the deodorizer 130 may operate in a power mode.

When the power mode is set, the deodorizer 130 may be operated to sterilize and deodorize air absorbed by a deodorizer while passing through a filter by the deodorizing fan 131.

In this case, in the power mode, the deodorizer 130 may repeatedly perform an operation at a period of 15 minutes such that the deodorizing fan 131 operates for 10 minutes and stops for 5 minutes. Accordingly, the deodorizer 130 may repeatedly operate to remove smell.

When the power mode is set, as the deodorizer 130 may operate to remove smell, a gas concentration in a refrigerator may be reduced.

When a gas concentration detected by the smell sensor 122 is reduced, the controller 110 may change a deodorizing mode to a normal automatic mode from a power mode at a second time T12. Accordingly, in a second period D2, the deodorizer 130 may repeatedly perform an operation at a period of 70 minutes such that the deodorizing fan 131 operates for 10 minutes and stops for 60 minutes.

In a normal automatic mode, the deodorizing fan 131 operates for 10 minutes and stops and, thus, deodorizing capability may be degraded.

When a new foodstuff is put in the refrigerator 1, the controller 110 may re-change a deodorizing mode to a power mode at a third time T13, and in a third period D3, the deodorizer 130 may operate in a power deodorizing mode to remove smell. Accordingly, a gas concentration in the refrigerator may be reduced again.

FIG. 10 is a diagram for explanation of a method of detecting and removing smell in a refrigerator according to an embodiment of the present invention.

The controller 110 may input a detected signal of the smell sensor 122 and determine smell intensity and, accordingly, change a deodorizing mode according to the smell intensity to control the deodorizer 130.

A detected signal input to the controller 110 from the smell sensor 122 may be a voltage value of 0 to 5 V. The controller 110 may change a voltage value of an input detected signal to resistance and determine smell intensity.

In the detected signal, as a gas concentration is increased and smell intensity is increased, a voltage value is increased, and as the gas concentration is reduced and smell intensity is reduced, a voltage value is reduced. Since the voltage value of the detected signal is changed to resistance to calculate a detected value, this means that, as the detected value is reduced, smell intensity is increased, and as the detected value is increased, smell intensity is reduced. In this case, the controller 110 may determine change in smell using a method of detecting a relative value. That is, the controller 110 may use a relative value but not an absolute value of smell and determine whether smell intensity is increased/strengthened or reduced/weakened compared with a previous stage. In order to determine the relative change, the controller 110 may change the voltage value of the detected value to resistance to calculate a detected value.

In this case, the controller 110 may calculate a reference value Ro and a current value Rs based on the detected value calculated from the detected signal and may determine change in smell according to a ratio of the reference value Ro to the current value Rs. The controller 110 may determine change between previous smell and current smell as a pollution level based on the ratio of the reference value Ro to the current value Rs and determine whether smell is strengthened or removed compared with a previous stage.

Accordingly, upon determining the current value Rs/the reference value Ro as a pollution level, the controller 110 may determine that, as a value of the pollution level is reduced, the pollution level is increased and smell is strengthened compared with a previous stage, and as a value of the pollution level is increased, the pollution level is reduced and smell is weakened compared with a previous stage.

For example, when a new foodstuff is input and smell is strengthened, a pollution level is increased, and when smell is removed by the deodorizer 130, the pollution level may be reduced.

The controller 110 may set a deodorizing mode to a power mode when a value of the current value Rs/the reference value Ro is a preset value or less. Here, the preset value may be set based on a gas concentration at which a user senses a strong smell.

The controller 110 may calculate an average during a predetermined time period and determine smell intensity based on the average based on the detected signal of the smell sensor 122, and change a current mode to a deodorizing mode. The refrigerator 1 may repeatedly supply chilled air according to circulation of a refrigerant, may allow a temperature in the refrigerator to reach a set target temperature, and may maintain the temperature. The refrigerator may have air flow and temperature that vary according to driving circulation and, accordingly, a value of a detected signal of the smell sensor 122 may be changed. Accordingly, the controller 110 may calculate an average and determine smell intensity.

The controller 110 may calculate a detected value in response to a continuously input detected signal and re-calculate the reference value Ro and the current value Rs using the detected value at a predetermined time frequency. In this case, the current value Rs may be an average of values measured within a recent predetermined time period and the reference value Ro may be an average of values measured within a previous predetermined time period except for a time in which a current value is calculated.

In this case, as described above, the reference value is re-calculated and varied at a predetermined period and not a fixed value. Accordingly, a reference value of first time and a reference value of second time are different and, accordingly, a calculated pollution level may be a relative value based on time. That is, as described above, the pollution level may be used to determine whether smell is strengthened or weakened but not to determine whether an absolute value is great or small.

For example, the controller 110 may calculate an average of detected values that are input from the smell sensor 122 during recent 10 minutes as the current value Rs and calculate an average of detected values of detected values that are input during the previous 10 minutes as a reference value.

The controller 110 may calculate an average of detected values during the previous one hour except for 10 minutes that are used to calculate the current value as the reference value Ro. That is, the previous one hour may be an average of previous one hour based on previous 10 minutes except for 10 minutes used to calculate the current value. Accordingly, the current value may be an average of detected values of detected signals that are input up to current time before 10 minutes and the reference value may be an average of detected values of detected signals that are input 10 minutes before from 70 minutes.

The controller 110 may calculate detected values in a unit of one minute and calculate the current value Rs and the reference value Ro in a unit of 10 minutes.

The controller 110 may calculate detected values in a unit of one minute and calculate an average of a plurality of detected values during 10 minutes, i.e., 10 detected values to calculate the current value Rs, and may calculate an average of detected values during one hour as a reference value. In this case, the current value Rs may be an average of detected values during 10 minutes and calculated in a unit of 10 minutes and, thus, the reference value Ro may be an average of current values calculated for one hour. That is, an average of six current values calculated for one hour may be calculated to calculate a reference value.

As illustrated in FIG. 10(a), the controller 110 may calculate an average of detected values that are measured during recent 10 minutes based on current time Tn, that is, in a second period P32 to current time Tn from time Tn−1 and set a current value Rs1 of current time Tn. The controller 110 may set a reference value Ro1 of the current time Tn as an average of detected signals that are measured in a first period P31 starting from time Tn−1 to time Tn−3, where time Tn−1 corresponds to a time before 10 minutes from the current time and time Tn−3 corresponds to a time before one hour from the current time.

As described above, since a current value and a reference value are re-calculated in a unit of ten minutes, a reference value Ro2 of time Tn+1 may be calculated as an average of detected values that are measured in a third period P33 starting from time Tn to time Tn−2 that corresponds to a time before one hour from time Tn at a time Tn+1 that corresponds to a time after 10 minutes from the current time.

In this case, current value Rs2 of time Tn+1 may be calculated as an average of detected values that are measured in a fourth period P34 between time Tn+1 and Tn.

As illustrated in FIG. 10(b), detected values R0 to R20 may be calculated in a unit of one minute and an average of the detected values may be calculated to calculate current values Rs1 and Rs2. Accordingly, an average of 10 detected values R0 to R9 that are measured in a second period P32 starting from to current time Tn may be calculated to calculate the current value Rs1 of Tn, and an average of 10 detected values R10 to R19 that are calculated in a fourth period P34 between Tn and Tn+1 may be calculated to calculate the current value Rs2.

The current value Rs1 of Tn and the current value Rs2 of Tn+1 may be calculated and, in this case, an average of a plurality of detected values calculated during the previous one hour, i.e., in the first period P31 between Tn−3 and Tn−1, that is, an average of 60 detected values calculated in the first period P31 may be calculated to calculate a reference value Ro1 of Tn. That is, an average of six current values calculated in the first period P31 may be calculated to calculate the reference value Ro1 of Tn.

The reference value Ro2 of Tn+1 may be calculated by calculating an average of 60 detected values calculated in the third period P33 between Tn−2 and Tn or an average of six current values.

An average during one hour before 10 minutes except for 10 minutes that is used to calculate a reference value is used to calculate a current value because the reference value Ro1 of Tn is calculated by calculating an average of the current value Rs0 of Tn−1 except for the current value Rs1 measured at Tn. The reference value Ro2 of Tn+1 may be calculated by calculating an average including the current value Rs1 measured at Tn.

The controller 110 may calculate change in smell based on the reference value Ro and the current value Rs that are re-calculated, that is, a pollution level according to time and compare a pollution level of time Tn and a pollution level of time Tn+1 to set a deodorizing mode. In this case, the pollution level of Tn may be Rs1/Ro1 and a pollution level of Tn+1 may be Rs2/Ro2.

When a pollution level of Rs/RO is a set value or less, the controller 110 may determine that a pollution level is increased and smell is strengthened compared with a previous stage and change a deodorizing mode to a power mode. The deodorizer 130 may operate according to a control command of the controller 110 such that a deodorizing fan absorbs air in a refrigerator. Accordingly, the absorbed air may pass through a filter to remove germs or impurities and may also remove smell.

In a power mode, the deodorizing fan may repeatedly perform an operation of stop for five minutes after an operation for 10 minutes for a set time period, according to a control command of the controller 110.

After the deodorizing mode is changed to the power mode, the smell sensor 122 may also continuously input a detected signal to the controller 110, and the controller 110 may calculate detected values of detected signals and calculate the reference value Ro and the current value Rs to determine a pollution level.

In this case, the controller 110 may change a deodorizing mode to a normal automatic mode when the current value Rs calculated during an operation in a power mode is greater than a reference value immediately before the deodorizing mode is changed to the power mode. In addition, when a pollution level calculated during an operation in a power mode is greater than a set value, the controller 110 may change a deodorizing mode to a normal automatic mode.

FIG. 11 is a flowchart illustrating a control method for deodorization of a refrigerator according to an exemplary embodiment of the present invention.

As illustrated in FIG. 11, during driving of the refrigerator 1, the smell sensor 122 may measure smell in the refrigerator and input a detected signal to the controller 110 (S310).

The controller 110 may detect a detected value of smell from the detected signal input from the smell sensor 122 and calculate a reference value and current value for determination of change in smell in the refrigerator (S320).

In this case, the controller 110 may change a voltage of the detected signal to resistance to calculate detected values and calculate the reference value and the current value using an average of the detected values. The controller 110 may calculate the detected values in a unit of one minute, calculate the current value using an average during recent 10 minutes, and calculate an average of detected values of previous one hour, that is, previous one hour except for 10 minutes used to calculate the current value.

The smell sensor 122 may measure a high voltage upon reacting with smell particles in the case of strong smell and measure a low voltage because the smell sensor 122 barely reacts with smell particles in the case of weak smell. Accordingly, since a detected value is resistance, the detected value is low in the case of strong smell and is high in the case of weak smell. The current and the reference value are also low in the case of strong smell and are also high in the case of weak smell.

The controller 110 may compare a ratio of the current value and the reference value with a set value to determine a pollution level in the refrigerator (S330). In this case, relative change of smell in the refrigerator may be determined using a value obtained by dividing the current value by the reference value as a pollution level.

That is, when a ratio of smell intensity for previous one hour and smell intensity during recent 10 minutes may be calculated and is less than a set value, it may be determined that smell is strong, in particular, that smell is strengthened compared with previous one hour, and when the ratio is greater than or equal to the set value, it may be determined that smell is weakened compared with previous 1 hour.

When the pollution level is less than a set value, the controller 110 may change a deodorizing mode to a power mode from a normal automatic mode (S340).

When the pollution level is greater than or equal to the set value, the controller 110 may maintain the normal automatic mode (S390). In this case, when the deodorizing mode is the power mode, if the pollution level is greater than or equal to the set value, it may be determined that smell is weakened and the controller 110 may change the deodorizing mode to the normal automatic mode.

The controller 110 may control the deodorizing fan 131 of the deodorizer 130 in response to change in the deodorizing mode and the deodorizing fan 131 may operate according to a control command and absorb air in the refrigerator (S350). Accordingly, the absorbed air may be sterilized and deodorized while passing through a filter in the deodorizer 130. The filter may include a sterilization filter and a deodorizing filter.

In this case, the deodorizing fan 131 may repeatedly perform an operation of being on standby during 60 minutes after an operation for about 10 minutes in a normal automatic mode and may repeatedly perform an operation of stop for five minutes after an operation for 10 minutes in a power mode.

The smell sensor 122 may continuously measure smell in the refrigerator (S360) and may input the smell to the controller 110.

As described above, the controller 110 may calculate detected values of detected signals and calculate a current value and a reference value according to the detected values.

After the deodorizing mode is changed to a power mode from a normal automatic mode, the controller 110 may compare the calculated current value with a reference value before the deodorizing mode is changed (S370).

In this case, when the current value is greater than the reference value before the deodorizing mode is changed, it may be determined that smell is weakened and the deodorizing mode may be changed to a normal automatic mode (S390).

When the current value is equal to or less than the reference value before the deodorizing mode is changed, the power mode may be maintained. When the power mode is maintained, the controller 110 may determine whether preset time elapses after the deodorizing mode is changed (S380). In this case, the controller 110 may set the preset time such that the power mode does not exceed maximum 5 hours.

Before the preset time elapses, the controller 110 may compare a ratio of the current value to the reference value, i.e. that is, a pollution level, with the set value to maintain or change the deodorizing mode.

When the set time elapses after the deodorizing mode is changed, the controller 110 may release the power mode and change the mode to an automatic mode (S390).

FIG. 12 is a diagram illustrating an example of a display unit of a refrigerator according to an exemplary embodiment of the present invention.

When a deodorizing mode is not set, the display unit 180 may not display information on the deodorizing mode, as illustrated in FIG. 12(a).

When the deodorizing mode is set, the display unit 180 may display an icon and a character about a normal automatic mode, in a normal automatic mode, as illustrated in FIG. 12(b), and when the power mode is set, the display unit 180 may display an icon and a character about a power mode, as illustrated in FIG. 12(c). For example, in the normal automatic mode, a deodorizing mode icon and 'Sensing' may be displayed, and in the power mode, a deodorizing mode icon and 'Power sensing' may be displayed.

In this case, according to setting of a deodorizing mode, an image, a character, and a special character corresponding to an icon as well as the icon may be displayed and at least one combination may be displayed. As necessary, a lamp corresponding thereto may be turned on.

As described above, when the deodorizing mode is changed, the controller 110 may control the display unit 180 to output information on the deodorizing mode.

As such, according to the present invention, a smell sensor may be used to measure smell in a refrigerator and, thus, a deodorizing mode may be automatically changed according to a degree of smell generated from a foodstuff to operate a deodorizer so as to remove the smell. Accordingly, user displeasure due to smell may be reduced. In addition, in the case of strong smell, the deodorizer may be operated so as to effectively use a filter with a limited lifetime.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A refrigerator comprising:
a smell sensor for detecting smell in the refrigerator;
a deodorizer for adsorbing, sterilizing, and deodorizing air in the refrigerator; and
a controller for calculating smell values based on the detected smell at the smell sensor, changing a deodorizing mode according to the detected smell, and controlling the deodorizer,
wherein the controller is configured to calculate an average of the smell values during a recent first time as a current value, to calculate an average of the smell values during a previous second time as a reference value, and to determine change in smell according to a ratio of the current value and the reference value,
upon determining that intensity of the smell is increased, the controller changes the deodorizing mode to a power mode from a normal automatic mode and controls the deodorizer to repeatedly operate for a set time period so as to remove smell in the refrigerator.

2. The refrigerator according to claim 1, wherein the controller calculates an average of the smell values and determines a change in the smell.

3. The refrigerator according to claim 1, wherein the controller calculates an average of the smell values during recent ten minutes as the current value and calculates an average of the smell values during previous one hour except for the ten minutes that are used to calculate the current value to calculate the reference value.

4. The refrigerator according to claim 1, wherein the controller compares a value obtained by dividing the current value by the reference value with a set value, determines that smell intensity is increased when the value is less than the set value, and determines that smell intensity is reduced when the value is greater than or equal to the set value.

5. The refrigerator according to claim 4, wherein the controller resets the deodorizing mode to the normal automatic mode when a ratio of the current value and the reference value set by the detected signals of the smell sensor is greater than the set value after the deodorizing mode is changed.

6. The refrigerator according to claim 1, wherein the controller determines whether smell intensity in the refrigerator is increased or reduced according to a method of detecting a relative value.

7. The refrigerator according to claim 1, wherein the controller continuously detects the smell values in response to the detected signals input from the smell sensor and calculates an average of the smell values in a unit of a predetermine time to re-calculate the current value and the reference value.

8. The refrigerator according to claim 7, wherein the controller calculates the smell values in a unit of one minute and recalculates the current value and the reference values in a unit of 10 minutes.

9. The refrigerator according to claim 8, wherein the controller changes the deodorizing mode to the power mode, and then compares the recalculated current value and a reference value calculated prior to setting of the power mode, and resets the deodorizing mode to the normal automatic mode upon determining that smell intensity is reduced.

10. The refrigerator according to claim 1, wherein the controller controls the deodorizer to repeatedly operate at a predetermined interval for the set time set to be greater than an operation time of the normal automatic mode when the power mode is set.

11. The refrigerator according to claim 10, wherein the deodorizer repeatedly performs an operation for the set time such that a deodorizing fan operates for 10 minutes and stops for 5 minutes in the power mode according to a control command of the controller and performs an operation of stopping during 60 minutes after an operation for about 10 minutes in the normal automatic mode.

12. The refrigerator according to claim 1, wherein the controller changes the deodorizing mode to the normal automatic mode from the power mode when the smell sensor malfunctions.

13. The refrigerator according to claim 1, wherein, when the smell sensor malfunctions and a door of the refrigerator is opened, the controller changes the deodorizing mode to the power mode and controls the deodorizer for a predetermined time period.

14. The refrigerator according to claim 1, wherein the smell sensor is a semiconductor-type gas sensor.

15. The refrigerator according to claim 1, wherein the smell sensor comprises any one of In2O2 and SnO2 as a detection material.

16. The refrigerator according to claim 15, wherein:
the smell sensor further comprises a device heater for heating the detection material,
the device heater has a heating temperature that is equal to or less than an ignition point of refrigerant gas in the refrigerator.

17. The refrigerator according to claim 15, wherein:
the smell sensor further comprises a sensor cap for protection of the detection material; and
the sensor cap comprises a hole for inlet and output of smell particles in air.

18. The refrigerator according to claim 1, wherein the smell sensor is formed of a non-toxic material.

19. The refrigerator according to claim 1, wherein the smell sensor is molded of urethane and waterproofed.

20. The refrigerator according to claim 1, wherein:
the deodorizer comprises a deodorizing fan, a sterilizing lamp, and a filter; and
the deodorizing fan is operated according to the deodorizing mode to blow the adsorbed air through the filter.

21. The refrigerator according to claim 20, wherein:
the filter comprises a photocatalyst filter and a deodorizing filter; and
particles in air adsorbed and sterilized by the photocatalyst filter and smell is removed through the deodorizing filter while the air adsorbed by the deodorizing fan is blown through the filter.

22. The refrigerator according to claim 20, wherein the filter comprises at least two deodorizing filters.

23. The refrigerator according to claim 1, further comprising a display unit for displaying at least one of an image, an icon, and a character corresponding to the deodorizing mode.

24. A method of controlling a refrigerator, the method comprising:
detecting smell in the refrigerator by a smell sensor;
calculating an average of smell values during a recent first time as a current value according to signals from the smell sensor and calculating an average of smell values during a previous second time except for the first time as a reference value;
determining change in the smell according to a value obtained by dividing the current value by the reference value;
changing a deodorizing mode to a power mode from a normal automatic mode when determining change in smell in the refrigerator and determining that smell intensity is increased;
repeatedly operating a deodorizer for a set time period to sterilize and deodorize air in the refrigerator according to the power mode;
re-detecting smell through the smell sensor during an operation in the power mode; and
releasing the power mode and resetting the normal automatic mode when smell intensity is reduced compared with a case before the power mode is set.

25. The method according to claim 24, wherein the smell values are calculated and an average of the smell values is calculated to determine change in the smell.

26. The method according to claim 24, further comprising recalculating the current value and the reference value at a third time interval to re-determine change in smell.

27. The method according to claim 26, further comprising calculating an average of the smell values during recent ten minutes as the current value and calculating an average of the smell values during previous one hour except for the ten minutes,
wherein the smell values are calculated at a one-minute interval and the current value and the reference value are re-calculated at a 10-minute interval.

28. The method according to claim 24, further comprising:
determining that smell intensity is increased to set the deodorizing mode to the power mode when a value obtained by dividing the current value by the reference value is less than a set value; and
determining that the smell intensity is reduced to set the deodorizing mode to the normal automatic mode when the value is greater than or equal to the set value.

29. The method according to claim 24, wherein the deodorizer repeatedly operates at a predetermined interval for the set time set to be greater than an operation time of the normal automatic mode when the power mode is set.

30. The method according to claim 29, wherein, when the power mode is set, a deodorizing fan included in the deodorizer repeatedly performs an operation of operating for 10 minutes and stopping for 5 minutes for the set time; and
when the normal automatic mode is set, the deodorizing fan repeatedly performs an operation of operating for 10 minutes and then stopping for 60 minutes.

31. The method according to claim 24, further comprising changing the deodorizing mode to the normal automatic mode when the smell sensor malfunctions.

32. The method according to claim 24, further comprising changing the deodorizing mode to the power mode and controlling the deodorizer for a predetermined time period when the smell sensor malfunctions and a door of the refrigerator is opened.

* * * * *